United States Patent
Furuta et al.

(10) Patent No.: US 10,526,450 B2
(45) Date of Patent: Jan. 7, 2020

(54) TERMINALLY MODIFIED IMIDE OLIGOMER, VARNISH, CURED PRODUCTS THEREOF, FILM, AND IMIDE PREPREG AND FIBER-REINFORCED COMPOSITE MATERIAL USING THESE

(71) Applicant: KANEKA CORPORATION, Osaka (JP)

(72) Inventors: Takefumi Furuta, Osaka (JP); Masahiko Miyauchi, College Station, TX (US); Rikio Yokota, Osaka (JP); Yuichi Ishida, Tokyo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/184,176

(22) Filed: Nov. 8, 2018

(65) Prior Publication Data

US 2019/0071541 A1 Mar. 7, 2019

Related U.S. Application Data

(63) Continuation of application No. PCT/JP2016/086141, filed on Dec. 6, 2016.

(30) Foreign Application Priority Data

May 9, 2016 (JP) ................. 2016-094029

(51) Int. Cl.

| C08G 73/10 | (2006.01) |
| C08J 5/24 | (2006.01) |
| C07D 401/14 | (2006.01) |
| C07D 487/04 | (2006.01) |
| C09D 179/08 | (2006.01) |
| C09D 7/20 | (2018.01) |

(52) U.S. Cl.
CPC ....... *C08G 73/1071* (2013.01); *C07D 401/14* (2013.01); *C07D 487/04* (2013.01); *C08J 5/24* (2013.01); *C09D 179/085* (2013.01); *C08G 2150/00* (2013.01); *C08J 2379/08* (2013.01); *C09D 7/20* (2018.01)

(58) Field of Classification Search
CPC .............. C08G 73/1071; C07D 401/14; C07D 487/04; C08J 5/24; C09D 179/085
See application file for complete search history.

(56) References Cited

U.S. PATENT DOCUMENTS

| 2011/0165809 A1* | 7/2011 | Miyauchi ............. C07D 209/48 442/392 |
| 2014/0011950 A1 | 1/2014 | Miyauchi et al. |
| 2016/0083618 A1 | 3/2016 | Miyauchi et al. |
| 2017/0152399 A1 | 6/2017 | Miyauchi et al. |
| 2018/0273798 A1 | 9/2018 | Miyauchi et al. |

FOREIGN PATENT DOCUMENTS

| JP | H3121132 A | 5/1991 |
| JP | 2006312699 A | 11/2006 |
| JP | 2012197237 A | 10/2012 |
| JP | 2014218632 A | 11/2014 |
| JP | 2015232117 A | 12/2015 |
| WO | 201027020 A1 | 3/2010 |
| WO | 2015174217 A1 | 11/2015 |

OTHER PUBLICATIONS

International Preliminary Report on Patentability issued in International Application No. PCT/JP2016/086141, dated Nov. 22, 2018 (5 pages).
International Search Report issued in International Application No. PCT/JP2016/086141, dated Jan. 24, 2017 (1 page).
Notice of Reasons for Allowance issued in corresponding Japanese Application No. 2018516337; dated Aug. 20, 2019 (4 pages).

* cited by examiner

*Primary Examiner* — Edward J Cain
(74) *Attorney, Agent, or Firm* — Osha Liang LLP

(57) ABSTRACT

A terminally modified imide oligomer is represented by a specific formula including a 2-phenyl-4,4'-diaminodiphenylether residue or a 4-phenoxy-1,3-diaminobenzene residue. A varnish is obtained by dissolving the terminally modified imide oligomer. A cured product is obtained by heat-curing the terminally modified imide oligomer, and a film including the cured product has a tensile elongation at break of 10% or more. An imide prepreg is obtained by impregnating fibers with the varnish and then drying the impregnated fibers. A fiber-reinforced composite material is obtained by layering and then heat-curing the imide prepreg.

14 Claims, No Drawings

TERMINALLY MODIFIED IMIDE OLIGOMER, VARNISH, CURED PRODUCTS THEREOF, FILM, AND IMIDE PREPREG AND FIBER-REINFORCED COMPOSITE MATERIAL USING THESE

TECHNICAL FIELD

One or more embodiments of the present invention relate to an terminally modified imide oligomer, a varnish obtained by dissolving the terminally modified imide oligomer in an organic solvent, a cured product of the terminally modified imide oligomer or the varnish, a film, an imide prepreg using the terminally modified imide oligomer or the varnish, and a fiber-reinforced composite material using the terminally modified imide oligomer or the varnish.

BACKGROUND

Aromatic polyimides have heat resistance which is of the highest level among polymeric substances and also exhibit superior mechanical characteristics, electrical characteristics, and the like. For these reasons, aromatic polyimides are used as a raw material in a wide range of fields, including aerospace and electrics/electronics.

However, aromatic polyimides generally have poor processability, and thus are particularly unsuited for use in melt molding and for use as a matrix resin in a fiber-reinforced composite material. For this reason, in cases where an aromatic polyimide is to be used as a matrix resin for a fiber-reinforced composite material, a polyimide capable of a thermal addition reaction is typically used. Specifically, a low-molecular-weight imide oligomer which has been terminally modified by a thermally-crosslinkable group is impregnated into fibers and then the resin is crosslinked and cured in a final step. In particular, an imide oligomer using 4-(2-phenylethynyl)phthalic anhydride as a terminal capping agent is known to provide excellent balance in terms of the moldability, heat resistance, and mechanical characteristics of a composite material.

For example, Patent Literature 1 discloses a terminally modified imide oligomer which is (a) synthesized from raw material compounds including (i) one or more aromatic diamines including 2-phenyl-4,4'-diaminodiphenylether and (ii) a 1,2,4,5-benzenetetracarboxylic acid, and (b) terminally modified by 4-(2-phenylethynyl)phthalic anhydride.

CITATION LIST

Patent Literature

[Patent Literature 1] International Publication No. 2010/027020

However, such conventional technology requires further improvement of its characteristics in terms of, for example, solubility in an organic solvent, in-solution storage stability, and moldability.

SUMMARY

One or more embodiments of the present invention provide (i) a terminally modified imide oligomer which is novel and has excellent solubility in an organic solvent, excellent in-solution storage stability, and excellent moldability, (ii) a varnish obtained by dissolving the terminally modified imide oligomer in an organic solvent, and (iii) a cured product, a film, an imide prepreg, and a fiber-reinforced composite material each of which (a) is produced with use of the terminally modified imide oligomer or the varnish and (b) has excellent thermal and mechanical characteristics, such as heat resistance, tensile modulus, tensile breaking strength, and tensile elongation at break.

The inventors found that, in a terminally modified imide oligomer which uses an aromatic diamine such as 2-phenyl-4,4'-diaminodiphenylether, copolymerization with 4-phenoxy-1,3-diaminobenzene makes it possible to provide (i) a terminally modified imide oligomer etc. which is novel and has excellent solubility in an organic solvent, excellent in-solution storage stability, and excellent moldability, and (ii) a cured product etc. which is made with use of the terminally modified imide oligomer and has excellent thermal and mechanical characteristics, such as heat resistance, tensile modulus, tensile breaking strength, and tensile elongation at break. The inventors thus arrived at one or more embodiments of the present invention including the following embodiments.

A terminally modified imide oligomer represented by the following general formula (1):

[Chem. 1]

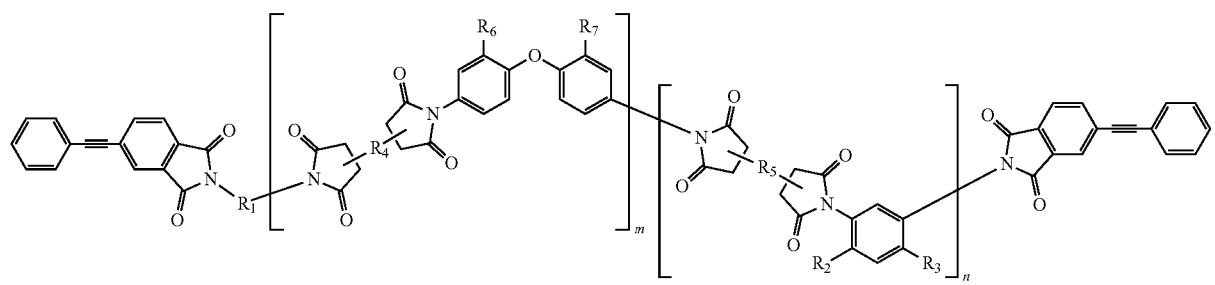

(1)

where: $R_1$ represents a divalent residue of an aromatic diamine selected from the group consisting of 2-phenyl-4,4'-diaminodiphenylether and 4-phenoxy-1,3-diaminobenzene; one of $R_2$ and $R_3$ represents a hydrogen atom and the other one of $R_2$ and $R_3$ represents a phenoxy group; $R_4$ and $R_5$ each represent a tetravalent residue of an aromatic tetracarboxylic acid and are identical or different; one of $R_6$ and $R_7$ represents a hydrogen atom and the other one of $R_6$ and $R_7$ represents a phenyl group; m and n satisfy the following: $m \geq 1$, $n > 0$, $1 < m+n \leq 10$, and $0.05 \leq m/(m+n) < 1$; and a sequence of repeating units may be a block sequence or a random sequence.

One or more embodiments of the present invention bring about the effect of making it possible to provide (i) a terminally modified imide oligomer which is novel and has excellent solubility in an organic solvent, excellent in-solution storage stability, and excellent moldability, (ii) a varnish obtained by dissolving the terminally modified imide oligomer in an organic solvent, and (iii) a cured product, a film, an imide prepreg, and a fiber-reinforced composite material each of which (a) is produced with use of the terminally modified imide oligomer or the varnish and (b) has excellent thermal and mechanical characteristics, such as heat resistance, tensile modulus, tensile breaking strength, and tensile elongation at break.

DETAILED DESCRIPTION OF EMBODIMENTS

The following description will discuss one or more embodiments of the present invention in detail. Any numerical range expressed as "A to B" in the present specification means "not less than A and not more than B (i.e., a range from A to B which includes both A and B)" unless otherwise stated.

[1. Terminally Modified Imide Oligomer]

A terminally modified imide oligomer in accordance with one or more embodiments of the present invention is represented by the following general formula (1):

[Chem. 2]

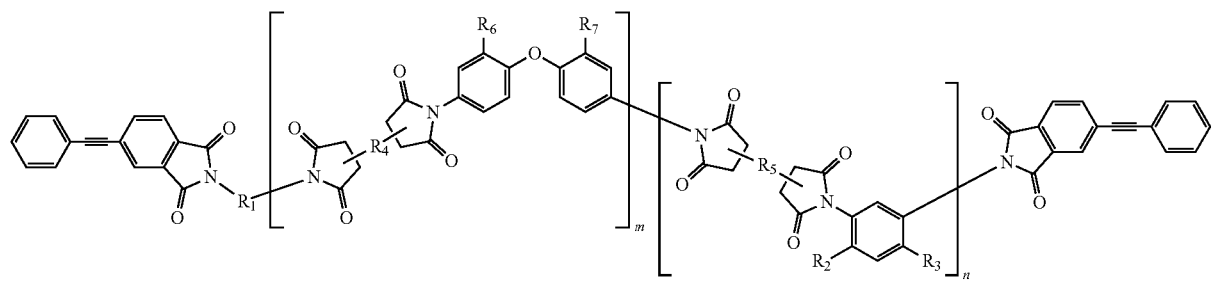

(1)

where: $R_1$ represents a divalent residue of an aromatic diamine selected from the group consisting of 2-phenyl-4,4'-diaminodiphenylether and 4-phenoxy-1,3-diaminobenzene; one of $R_2$ and $R_3$ represents a hydrogen atom and the other one of $R_2$ and $R_3$ represents a phenoxy group; $R_4$ and $R_5$ each represent a tetravalent residue of an aromatic tetracarboxylic acid and are identical or different; one of $R_6$ and $R_7$ represents a hydrogen atom and the other one of $R_6$ and $R_7$ represents a phenyl group; m and n satisfy the following: $m \geq 1$, $n > 0$, $1 < m+n \leq 10$, and $0.05 \leq m/(m+n) < 1$; and a sequence of repeating units may be a block sequence or a random sequence.

The divalent residue of the aromatic diamine refers to an aromatic organic group existing between two amino groups in the aromatic diamine. The tetravalent residue of the aromatic tetracarboxylic acid refers to an aromatic organic group surrounded by four carbonyl groups in the aromatic tetracarboxylic acid. Here, "aromatic organic group" refers to an organic group having an aromatic ring. The aromatic organic group may be preferably an organic group having 4 to 30 carbon atoms, more preferably an organic group having 4 to 18 carbon atoms, and even more preferably an organic group having 4 to 12 carbon atoms. The aromatic organic group may be preferably a group having 6 to 30 carbon atoms and including hydrogen, more preferably a group having 6 to 18 carbon atoms and including hydrogen, and even more preferably a group having 6 to 12 carbon atoms and including hydrogen.

In a terminally modified imide oligomer in accordance with one or more embodiments of the present invention, $R_1$ and/or both of $R_2$ and $R_3$ can have respective structures derived from 4-phenoxy-1,3-diaminobenzene. $R_1$ and/or both of $R_6$ and $R_7$ can have respective structures derived from 2-phenyl-4,4'-diaminodiphenylether.

$R_2$ and $R_3$ can also be described as being different ones of the group consisting of a hydrogen atom and a phenoxy group. In a case where $n > 1$, the terminally modified imide oligomer may optionally contain both (i) a repeating unit in which $R_2$ is the phenoxy group and $R_3$ is the hydrogen atom and (ii) a repeating unit in which $R_2$ is the hydrogen atom and $R_3$ is the phenoxy group.

$R_4$ and $R_5$ are each a tetravalent residue of an aromatic tetracarboxylic acid and may be identical or different. In the present specification, the term "aromatic tetracarboxylic acid" encompasses an aromatic tetracarboxylic acid, an aromatic tetracarboxylic dianhydride, and an acid derivative (such as an ester and a salt) of an aromatic tetracarboxylic acid.

$R_6$ and $R_7$ can also be described as being different ones of the group consisting of a hydrogen atom and a phenyl group. In a case where $m > 1$, the terminally modified imide oligomer may optionally contain a repeating unit in which $R_6$ is the phenyl group and $R_7$ is the hydrogen atom and a repeating unit in which $R_6$ is the hydrogen atom and $R_7$ is the phenyl group.

$R_1$ to $R_7$ may be different or identical in each repeating unit.

In the present specification, the expression "a sequence of repeating units may be a block sequence or a random sequence" means that the repeating units may be block polymerized or may be randomly polymerized.

In one or more embodiments, the tetravalent residue of the aromatic tetracarboxylic acid is preferably selected from residues derived from a 1,2,4,5-benzenetetracarboxylic acid. Here, the term "1,2,4,5-benzenetetracarboxylic acid" encompasses 1,2,4,5-benzenetetracarboxylic acid, 1,2,4,5-benzenetetracarboxylic dianhydride (PMDA), and an acid derivative (such as an ester and salt) of 1,2,4,5-benzenetetracarboxylic acid. In particular, the 1,2,4,5-benzenetetracarboxylic dianhydride is optimal. In a case where $R_4$ and $R_5$ are each a residue of a 1,2,4,5-benzenetetracarboxylic acid, the imide oligomer is represented by the following general formula (2):

[Chem. 3]

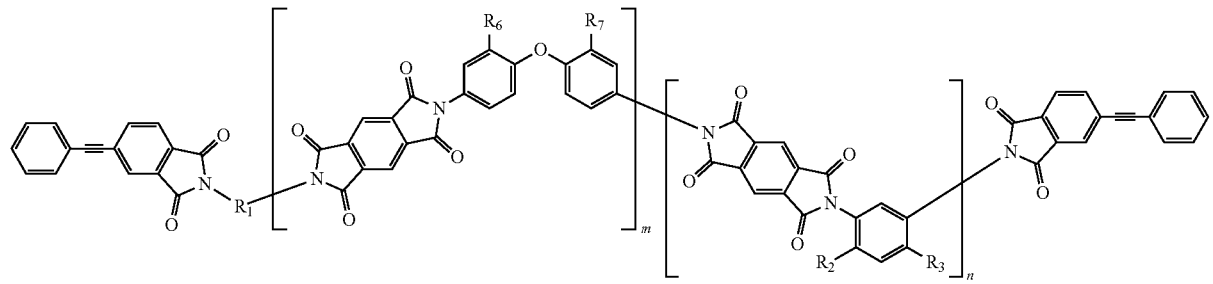

(2)

where: $R_1$ represents a divalent residue of an aromatic diamine selected from the group consisting of 2-phenyl-4,4'-diaminodiphenylether and 4-phenoxy-1,3-diaminobenzene; one of $R_2$ and $R_3$ represents a hydrogen atom and the other one of $R_2$ and $R_3$ represents a phenoxy group; one of $R_6$ and $R_7$ represents a hydrogen atom and the other one of $R_6$ and $R_7$ represents a phenyl group; m and n satisfy the following: $m \geq 1$, $n > 0$, $1 < m+n \leq 10$, and $0.05 \leq m/(m+n) < 1$; and a sequence of repeating units may be a block sequence or a random sequence.

In the terminally modified imide oligomer in accordance with one or more embodiments of the present invention, a 1,2,4,5-benzenetetracarboxylic acid may be used alone as the aromatic tetracarboxylic acid, or part of the 1,2,4,5-benzenetetracarboxylic acid may be substituted with another aromatic tetracarboxylic acid compound, to the extent that the effect of one or more embodiments of the present invention is still brought about. Examples of the "another aromatic tetracarboxylic acid compound" include 3,3',4,4'-biphenyltetracarboxylic dianhydride (s-BPDA), 3,3',4,4'-benzophenonetetracarboxylic dianhydride (BTDA), 2,3,3',4'-biphenyltetracarboxylic dianhydride (a-BPDA), 2,2',3,3'-biphenyltetracarboxylic dianhydride (i-BPDA), 2,2-bis(3,4-dicarboxyphenyl)methane dianhydride, bis(3,4-carboxyphenyl)ether dianhydride, and 1,2,3,4-benzenetetracarboxylic dianhydride.

In a terminally modified imide oligomer in accordance with one or more embodiments of the present invention, the 2-phenyl-4,4'-diaminodiphenylether or the 4-phenoxy-1,3-diaminobenzene may be partially substituted with another aromatic diamine compound. Examples of the "another aromatic diamine compound" include 1,4-diaminobenzene, 1,3-diaminobenzene, 1,2-diaminobenzene, 2,6-diethyl-1,3-diaminobenzene, 4,6-diethyl-2-methyl-1,3-diaminobenzene, 3,5-diethyltoluene-2,6-diamine, 4,4'-diaminodiphenylether (4,4'-ODA), 3,4'-diaminodiphenylether (3,4'-ODA), 3,3'-diaminodiphenylether, 2-phenyl-3',4-diaminodiphenylether, 2-phenyl-2',4-diaminodiphenylether, 3-phenyl-4,4'-diaminodiphenylether, 3,3'-diaminobenzophenone, 4,4'-diaminobenzophenone, 3,3'-diaminodiphenylmethane, 4,4'-diaminodiphenylmethane, bis(2,6-diethyl-4-aminophenyl)methane, 4,4'-methylene-bis(2,6-diethylaniline), bis(2-ethyl-6-methyl-4-aminophenyl)methane, 4,4'-methylene-bis(2-ethyl-6-methylaniline, 2,2-bis(3-aminophenyl)propane, 2,2-bis(4-aminophenyl)propane, 1,3-bis(4-aminophenoxy)benzene, 1,3-bis(3-aminophenoxy)benzene, 1,4-bis(4-aminophenoxy)benzene, 1,4-bis(3-aminophenoxy)benzene, benzidine, 3,3'-dimethylbenzidine, 2,2-bis(4-aminophenoxy)propane, 2,2-bis(3-aminophenoxy)propane, 2,2-bis[4'-(4"-aminophenoxy)phenyl]hexafluoropropane, 9,9-bis(4-aminophenyl)fluorene, and 9,9-bis(4-(4-aminophenoxy)phenyl)fluorene. These compounds may be used alone or in combination of two or more.

As described above, in the general formula (1), m and n satisfy the following: $m \geq 1$, $n > 0$, $1 < m+n \leq 10$, and $0.05 \leq m/(m+n) < 1$. It may be preferable that m and n satisfy the following: $0.25 \leq m/(m+n) < 1$. It may be more preferable that m and n satisfy the following: $0.5 \leq m/(m+n) < 1$. It may be preferable for m and n to satisfy the above inequalities because doing so causes the terminally modified imide oligomer in accordance with one or more embodiments of the present invention to have even better in-solution storage stability. m and n may satisfy the following: $1 \leq m \leq 5$, $0 < n \leq 5$, $1 < m+n \leq 10$, and $0.25 \leq m/(m+n) < 1$.

A terminally modified imide oligomer in accordance with one or more embodiments of the present invention may be preferably a solid (in powder form) at a normal temperature (23° C.).

In a terminally modified imide oligomer in accordance with one or more embodiments of the present invention, 4-(2-phenylethynyl)phthalic anhydride may be preferably used as an unsaturated acid anhydride for terminal modification (end cap). In other words, a terminally modified imide oligomer in accordance with one or more embodiments of the present invention may be preferably an imide oligomer which (i) has an imide bond in its main chain and (ii) has, at a terminal (preferably, at both terminals), an addition-polymerizable unsaturated terminal group derived from 4-(2-phenylethynyl)phthalic anhydride. Furthermore, the 4-(2-phenylethynyl)phthalic anhydride may be preferably used at a proportion in a range of 5 mol % to 200 mol % with respect to a total amount of acids, and particularly preferably used at a proportion in a range of 5 mol % to 150 mol % with respect to the total amount of acids.

A terminally modified imide oligomer in accordance with one or more embodiments of the present invention may be preferably an imide oligomer obtained by (i) preparing the following substances (a) to (c) in an amount such that a total amount of dicarboxylic acid groups and a total amount of primary amino groups are substantially equal and then (ii) reacting the substances (a) to (c) in the presence or absence of an organic solvent: (a) an aromatic tetracarboxylic acid (for example, a 1,2,4,5-benzenetetracarboxylic acid such as 1,2,4,5-benzenetetracarboxylic dianhydride); (b) 2-phenyl-4,4'-diaminodiphenylether and 4-phenoxy-1,3-diaminobenzene; and (c) 4-(2-phenylethynyl)phthalic anhydride for introducing an unsaturated terminal group into the terminally modified imide oligomer in accordance with one or more embodiments of the present invention (in the case of mutually adjacent dicarboxylic acid groups, it is considered that there is 1 mol of an acid anhydride group per 2 mol of a carboxyl group). A method of producing a terminally modified imide oligomer in accordance with one or more embodiments of the present invention is discussed later in detail.

Having the above constitution allows the terminally modified imide oligomer in accordance with one or more embodiments of the present invention to have excellent solubility in an organic solvent, excellent in-solution storage stability, and excellent moldability, and makes it easy to form the terminally modified imide oligomer into a film by heat molding. In the present specification, the term "moldability" takes into account high-temperature melt flowability and low melt viscosity. The above constitution makes it possible to provide a terminally modified imide oligomer and a varnish which are novel and have (i) excellent thermal characteristics, such as heat resistance of a cured product and (ii) excellent mechanical characteristics, such as tensile modulus, tensile breaking strength, and tensile elongation at break, as well as cured product etc. of the terminally modified imide oligomer or the varnish. This will be discussed below along with a comparison to conventional technology.

The terminally modified imide oligomer described in Patent Literature 1 dissolves, in N-methyl-2-pyrrolidone which is at room temperature, in an amount of not less than 30 weight %, but a varnish containing a terminally modified imide oligomer having a high molecular weight will gelate in a matter of days. With regards to this, Patent Literature 1 discloses that copolymerizing the terminally modified imide oligomer of Patent Literature 1 with small amounts of, for example, 9,9-bis(4-(4-aminophenoxy)phenyl)fluorene, 9,9-bis(4-aminophenyl)fluorene, and/or 1,3-diaminobenzene as aromatic diamines in addition to 2-phenyl-4,4'-diaminodiphenylether causes the terminally modified imide oligomer to have excellent in-solution storage stability. This is because the copolymerization increases randomness of molecular chains of the imide oligomer, and agglutination between imide oligomers is suppressed by the bulky three-dimensional structures of 9,9-bis(4-(4-aminophenoxy)phenyl)fluorene and 9,9-bis(4-aminophenyl)fluorene. Furthermore, an increased copolymerization ratio of such aromatic diamines brings about an effect of increasing rigidity of molecular chains of the imide oligomer and improving a glass transition temperature (Tg) of cured products.

However, a high copolymerization ratio of such aromatic diamines causes a decrease in the solubility of the imide oligomer itself and thus makes it difficult to obtain a varnish having excellent storage stability. Furthermore, melt flowability of the imide oligomer at high temperatures decreases, resulting in a decrease in molding processability and a marked decrease in elongation at break of heat-cured products. It is noted that in order to improve the elongation at break of a heat-cured product of such a terminally modified imide oligomer, there exists a method of improving the number of repeating units in the terminally modified imide oligomer, as disclosed by Hergenrother, P. M.; Smith Jr, J. G., Polymer, 1994, 35 (22), 4857-4864. However, such a method causes a further decrease in the solubility and high-temperature melt flowability of the terminally modified imide oligomer. As such, it has been difficult conventionally to produce a varnish having excellent storage stability and a terminally modified imide oligomer having excellent molding processability.

In other words, with conventional technology such as that described above, an increase in the copolymerization ratio of aromatic diamines in the imide oligomer is accompanied by an increase in the rigidity of molecular chains of the imide oligomer. When this happens, molecules of the imide oligomer become prone to agglutination, and there is a trend of deterioration in, for example, the solubility and high-temperature melt flowability of the imide oligomer. Because of this, there has been the need for further improvements in the characteristics of conventional technology.

In contrast, in one or more embodiments of the present invention, due to the effect of 4-phenoxy-1,3-diaminobenzene, it is possible to provide a terminally modified imide oligomer which is novel and has excellent solubility in an organic solvent, excellent in-solution storage stability, and excellent moldability. Although 4-phenoxy-1,3-diaminobenzene does have a rigid 1,3-diaminobenzene structure, the presence of a bulky phenoxy group makes it possible to suppress agglutination between imide oligomer molecules. This makes it possible to achieve an imide oligomer having excellent solubility in an organic solvent, excellent in-solution storage stability, and excellent moldability. It is also possible to provide a varnish obtained by dissolving the terminally modified imide oligomer in an organic solvent, as well as a cured product which is made with use of the terminally modified imide oligomer and has excellent thermal and mechanical characteristics such as heat resistance, tensile modulus, tensile breaking strength, and tensile elongation at break. Furthermore, by using such a varnish to impregnate fibers, it is possible to obtain an imide prepreg which has excellent storability and handleability, and which exhibits excellent adhesiveness with other layers of prepreg when layered. Furthermore, by layering the imide prepreg and heat molding the layers, it is possible to obtain a fiber-reinforced composite material which has high heat resistance. It is thought that the asymmetric structures of 2-phenyl-4,4'-diaminodiphenylether and 4-phenoxy-1,3-diaminobenzene also bring about an advantageous effect in one or more embodiments of the present invention.

A terminally modified imide oligomer in accordance with one or more embodiments of the present invention can preferably dissolve, in an organic solvent which is at room temperature, so as to achieve a solid content concentration of not less than 30 weight %, and can more preferably dissolve, in an organic solvent which is at room temperature, so as to achieve a solid content concentration of not less than 35 weight %. Examples of the organic solvent include N-methyl-2-pyrrolidone (NMP), N,N-dimethylacetamide (DMAc), N,N-diethylacetamide, N-methylcaprolactam, γ-butyrolactone (GBL), and cyclohexanone. A terminally modified imide oligomer in accordance with one or more embodiments of the present invention can preferably dissolve, in NMP which is at room temperature, so as to achieve a solid content of not less than 30 weight %.

A terminally modified imide oligomer in accordance with one or more embodiments of the present invention has a minimum melt viscosity which is preferably not more than 10000 Pa·sec, more preferably not more than 5000 Pa·sec, and even more preferably not more than 3000 Pa·sec. Such a minimum melt viscosity may be preferable because it allows the terminally modified imide oligomer in accordance with one or more embodiments of the present invention to have excellent moldability. Such a minimum melt viscosity may also be preferable because with such a minimum melt viscosity, when an organic solvent in a prepreg is removed from the prepreg at a high temperature during molding of a fiber-reinforced composite material, the remaining imide oligomer is allowed to melt and impregnate space between fibers. Note that in the present specification, the "minimum melt viscosity" is measured by a method described later in the Examples.

A terminally modified imide oligomer in accordance with one or more embodiments of the present invention may be obtained by mixing terminally modified imide oligomers having differing molecular weights. A terminally modified imide oligomer in accordance with one or more embodiments of the present invention may be mixed with another soluble polyimide or thermoplastic polyimide. The thermoplastic polyimide is not limited in terms of type etc., and may be any polyimide which softens when heated and which is commercially available.

[2. Method of Producing Terminally Modified Imide Oligomer]

A method of producing a terminally modified imide oligomer in accordance with one or more embodiments of the present invention is not particularly limited, and any method may be used. Examples are described below.

The following substances are used in an amount such that a total amount of acid anhydride groups (in the case of mutually adjacent dicarboxylic acid groups, it is considered that there is 1 mol of an acid anhydride group per 2 mol of a carboxyl group) and a total amount of amino groups in all components is substantially equal: the aromatic tetracarboxylic acid; aromatic diamines including 2-phenyl-4,4'-diaminodiphenylether and 4-phenoxy-1,3-diaminobenzene; and 4-(2-phenylethynyl)phthalic anhydride. The components are polymerized in an organic solvent (described later) at a reaction temperature of not more than approximately 100° C., particularly not more than 80° C., so that an amide acid oligomer (an oligomer having an amide-acid bond, also known as an amic acid oligomer) is produced. Next, the amide acid oligomer is dehydrated and cyclized by a method of adding an imidization agent at a low temperature of approximately 0° C. to 140° C., or by a method of heating the amide acid oligomer to a high temperature of 140° C. to 275° C. This makes it possible to obtain an imide oligomer (terminally modified imide oligomer) having 4-(2-phenylethynyl)phthalic anhydride residue at its terminal(s). As described above, a 1,2,4,5-benzenetetracarboxylic acid (particularly, 1,2,4,5-benzenetetracarboxylic dianhydride) may be preferably used as the aromatic tetracarboxylic acid.

A method of producing a terminally modified imide oligomer in accordance with one or more embodiments of the present invention may be, for example, as follows. First, aromatic diamines including 2-phenyl-4,4'-diaminodiphenylether and 4-phenoxy-1,3-diaminobenzene are homogenously dissolved in an organic solvent (described later), and thereafter one or more aromatic tetracarboxylic dianhydrides including 1,2,4,5-benzenetetracarboxylic dianhydride are added to the obtained solution and dissolved homogenously therein so as to obtain a reaction solution. Thereafter, the reaction solution is stirred at a reaction temperature of approximately 5° C. to 60° C. for approximately 1 minute to 180 minutes. Next, 4-(2-phenylethynyl)phthalic anhydride is added to the reaction solution and homogenously dissolved therein. Thereafter, the reaction solution is caused to react while being stirred at a reaction temperature of approximately 5° C. to 60° C. for approximately 1 minute to 180 minutes, so as to produce the above-described terminally modified amide acid oligomer. Thereafter, the reaction solution is stirred at 140° C. to 275° C. for 5 minutes to 24 hours so as to cause the amide acid oligomer to undergo an imidization reaction. In this way, a terminally modified imide oligomer in accordance with one or more embodiments of the present invention can be obtained. If necessary, a terminally modified imide oligomer in accordance with one or more embodiments of the present invention may be obtained by cooling the reaction solution to approximately room temperature after the terminally modified amide acid oligomer undergoes the imidization reaction. It is suitable to carry out the reactions in a manner so that some or all of the reaction steps are carried out in an inert gas (such as nitrogen gas or argon gas) atmosphere or in a vacuum.

Examples of the organic solvent include N-methyl-2-pyrrolidone (NMP), N,N-dimethylacetamide (DMAc), N,N-diethylacetamide, N-methylcaprolactam, γ-butyrolactone (GBL), and cyclohexanone. These solvents may be used alone or in combination of two or more. In selecting these solvents, it is possible to apply known techniques regarding soluble polyimides.

If necessary, the terminally modified imide oligomer in accordance with one or more embodiments of the present invention produced as above may be isolated as a product in powder form after pouring the reaction solution into, for example, water. The terminally modified imide oligomer in accordance with one or more embodiments of the present invention may be used in powder form. Alternatively, if necessary, the terminally modified imide oligomer in accordance with one or more embodiments of the present invention may be used after the product in powder form is dissolved in the organic solvent.

[3. Varnish]

A varnish in accordance with one or more embodiments of the present invention is obtained by dissolving the terminally modified imide oligomer in an organic solvent. A varnish in accordance with one or more embodiments of the present invention can be obtained by dissolving the terminally modified imide oligomer in powder form into an organic solvent as described above. Alternatively, the varnish may be obtained as a solution composition containing the terminally modified imide oligomer, by using the above-described reaction solution as is, or in a concentrated or diluted state as necessary. The above-described solvents can be used as the organic solvent.

There is almost no risk of the varnish undergoing hydrolysis. This makes it possible to store the varnish stably for a longer period without, for example, a decrease in viscosity, as compared to an amide acid oligomer varnish. With regards to a solvent to be used for long-term storage of the varnish in accordance with one or more embodiments of the present invention, in order to prevent gelation, it may be desirable to use an amide solvent such as N-methyl-2-pyrrolidone, which is a more favorable solvent.

[4. Cured Product]

A cured product in accordance with one or more embodiments of the present invention may be obtained by heat-curing the above terminally modified imide oligomer or by heat-curing the above varnish. Note that heating the terminally modified imide oligomer or the varnish causes (i) the terminally modified imide oligomer to have a high molecular weight due to a reaction between the 4-(2-phenylethynyl) phthalic anhydride residue at a terminal(s) of the terminally modified imide oligomer and other molecules and (ii) curing of the terminally modified imide oligomer. It is thought that, in the reaction, a triple bond in the 4-(2-phenylethynyl) phthalic anhydride residue and a double bond and a single bond derived from the triple bond contribute to causing the structure of the terminally modified imide oligomer to become very complex after the reaction.

The form of a cured product in accordance with one or more embodiments of the present invention is not particularly limited. The cured product in accordance with one or more embodiments of the present invention may be molded to a desired form by use of any method. Examples of the form of the cured product in accordance with one or more embodiments of the present invention include two-dimensional and three-dimension forms obtained by molding, such as a film form, a sheet form, a rectangular parallelepiped form, and a rod form. For example, in a case where the cured product is to be in the form of a film, it is possible to apply the terminally modified imide oligomer varnish to a supporting body and heat-cure the varnish at 280° C. to 500° C. for 5 minutes to 200 minutes so as to obtain a film. In other words, one or more embodiments of the present invention encompasses a film consisting of the cured product in accordance with one or more embodiments of the present invention (that is, a cured product in the form of a film).

Alternatively, a cured product in accordance with one or more embodiments of the present invention can be obtained by (i) filling a mold with the terminally modified imide oligomer in powder form, (ii) molding the terminally modified imide oligomer into a preform by use of compression molding at 10° C. to 280° C. and 1 kg/cm$^2$ to 1000 kg/cm$^2$ for approximately 1 second to 100 minutes, and (iii) heating the preform at 280° C. to 500° C. for approximately 10 minutes to 40 hours.

The cured product (or the film) in accordance with one or more embodiments of the present has a tensile elongation at break which is preferably not less than 10% and more preferably not less than 15%. Having a tensile elongation at break falling within the above ranges allows the cured product or film to have even better mechanical characteristics. Note that in the present specification, the "tensile elongation at break" is measured by a method described later in the Examples.

The cured product in accordance with one or more embodiments of the present invention has a tensile modulus which is preferably not less than 2.5 GPa and more preferably not less than 2.8 GPa. Note that in the present specification, the "tensile modulus" is measured by a method described later in the Examples.

The cured product in accordance with one or more embodiments of the present invention has a tensile breaking strength which is preferably not less than 120 MPa and more preferably not less than 125 MPa. Note that in the present specification, the "tensile breaking strength" is measured by a method described later in the Examples.

Having a tensile elongation at break, a tensile modulus, and/or a tensile breaking strength which fall into the above ranges allows the cured product in accordance with one or more embodiments of the present invention to have even better mechanical characteristics.

The cured product in accordance with one or more embodiments of the present invention has a glass transition temperature (Tg) which is preferably not less than 300° C. and more preferably not less than 350° C. Having a glass transition temperature that falls in the above ranges allows the cured product in accordance with one or more embodiments of the present invention to have even better heat resistance. Note that in the present specification, the "glass transition temperature" is measured by a method described later in the Examples.

[5. Imide Prepreg]

An imide prepreg in accordance with one or more embodiments of the present invention is obtained by impregnating fibers with the above-described varnish and then drying the fibers thus impregnated. The imide prepreg in accordance with one or more embodiments of the present invention can be obtained, for example, in the following manner.

First, a terminally modified imide oligomer solution composition (varnish) is prepared by dissolving the terminally modified imide oligomer in powder form into an organic solvent, or by using the reaction solution as is, or in a concentrated or diluted state as necessary. The imide prepreg can then be obtained by, for example, impregnating the terminally modified imide oligomer varnish, having an appropriately adjusted concentration, into fibers provided in a planar form and aligned unidirectionally, or into a fiber fabric, and then drying the fibers or fiber fabric thus impregnated in a dryer at 20° C. to 180° C. for 1 minutes to 20 hours.

At this time, a content of resin adhering to the fibers or fiber fabric may be preferably 10 weight % to 60 weight %, more preferably 20 weight % to 50 weight %, and even more preferably 30 weight % to 50 weight %. Note that in the present specification, the content of resin refers to a weight of the terminally modified imide oligomer (resin) adhering to the fibers or the fiber fabric with respect to the combined weight of (i) the terminally modified imide oligomer (resin) and (ii) the fibers or fiber fabric.

In one or more embodiments, an amount of the organic solvent adhering to the fibers or fiber fabric is preferably 1 weight % to 30 weight %, more preferably 5 weight % to 25 weight %, and even more preferably 5 weight % to 20 weight %, with respect to the total weight of the imide prepreg. In a case where the amount of the organic solvent adhering to the fibers or the fiber fabric falls within the above ranges, the imide prepreg can be easily handled during layering. Further, outflow of resin is prevented during high-temperature molding of a composite material, which makes it possible to produce a fiber-reinforced composite material exhibiting excellent mechanical strength.

Examples of the fibers include, inorganic fiber such as carbon fiber, glass fiber, metal fiber, ceramic fiber, as well as organic synthetic fiber such as polyamide fiber, polyester-based fiber, polyolefin-based fiber, and novoloid fiber. These types of fiber may be used alone or in combination of two or more.

In particular, in order for the fiber-reinforced composite material produced from the imide prepreg to have excellent mechanical characteristics, it may be desirable to use carbon fiber as the fibers. The carbon fiber is not particularly limited, provided that it is a material which (i) has a carbon content in a range of 85 weight % to 100 weight % and (ii) is in the form of continuous fibers whose structure is at least partially a graphite structure. Examples of the carbon fiber include polyacrylonitrile (PAN) based carbon fiber, rayon-based carbon fiber, lignin-based carbon fiber, and pitch-based carbon fiber. Out of these, PAN-based carbon fiber, pitch-based carbon fiber, and the like may be preferable, because such carbon fibers are versatile, inexpensive, and have high strength. The carbon fiber typically undergoes sizing and may be used as is after sizing. If necessary, it is also possible to perform removal by use of, for example, an organic solvent. It may be preferable to spread the fibers of a carbon fiber bundle in advance by use of air or a roller, and then impregnate the resin or a resin solution between individual fibers.

The form of the fiber material constituting the imide prepreg in accordance with one or more embodiments of the present invention is not particularly limited. Possible examples include unidirectional (UD) fibers and continuous fibers structures obtained by weaving (plain weaving, satin weaving, etc.) or knitting. The form of the fiber material can be selected as appropriate in accordance with the purpose of use. These forms may be used alone on in combination.

[6. Fiber-Reinforced Composite Material]

A fiber-reinforced composite material in accordance with one or more embodiments of the present invention may be obtained by layering and then heat-curing the imide prepreg. The fiber-reinforced composite material may alternatively be obtained by layering and then heat-curing fibers to which the terminally modified imide oligomer is adhered, the terminally modified imide oligomer being in powder form. As described above, heat-curing causes the terminally modified imide oligomer to have a high molecular weight and a very complex structure. A fiber-reinforced composite material in accordance with one or more embodiments of the present invention can be obtained, for example, in the following manner.

The fiber-reinforced composite material can be obtained by layering the imide prepreg in a predetermined number of layers and then using an autoclave, a hot press, or the like to heat-cure the imide prepreg at a temperature of 280° C. to 500° C. and a pressure of 1 kg/cm² to 1000 kg/cm² for approximately 10 minutes to 40 hours. Alternatively, instead of using the imide prepreg, the fiber-reinforced composite material can be obtained as a laminate produced by layering fibers to which the terminally modified imide oligomer in powder form is adhered and then heat-curing the fibers in the above manner.

A fiber-reinforced composite material in accordance with one or more embodiments of the present invention has a glass transition temperature (Tg) which is preferably not less than 300° C. and more preferably not less than 350° C. Having a glass transition temperature that falls in the above ranges allows the fiber-reinforced composite material in accordance with one or more embodiments of the present invention to have even better heat resistance. Note that in the present specification, the "glass transition temperature" is measured by a method described later in the Examples.

A fiber-reinforced composite material structure may be obtained by inserting the imide oligomer molded into film form or the imide prepreg between (i) the fiber-reinforced composite material and (ii) a different material, and then heating and melting the imide oligomer or the imide prepreg to produce an integrated structure. The different material is not particularly limited and can be any material ordinarily used in the art. Examples of the different material include a metal material having, for example, a honeycomb-like shape, and a core material having, for example, a sponge-like shape.

[7. Uses]

The terminally modified imide oligomer, cured product thereof, and the like can be used in a wide range of fields requiring easy moldability and high heat resistance, such as the fields of aircraft and space industry devices.

The present invention is not limited to the above embodiments, but can be altered by a skilled person in the art within the scope of the claims. The present invention also encompasses, in its technical scope, any embodiment derived by combining technical means disclosed in differing embodiments.

It is also possible for one or more embodiments of the present invention to be composed as follows.

[1] A terminally modified imide oligomer represented by the following general formula (1):

[Chem. 4]

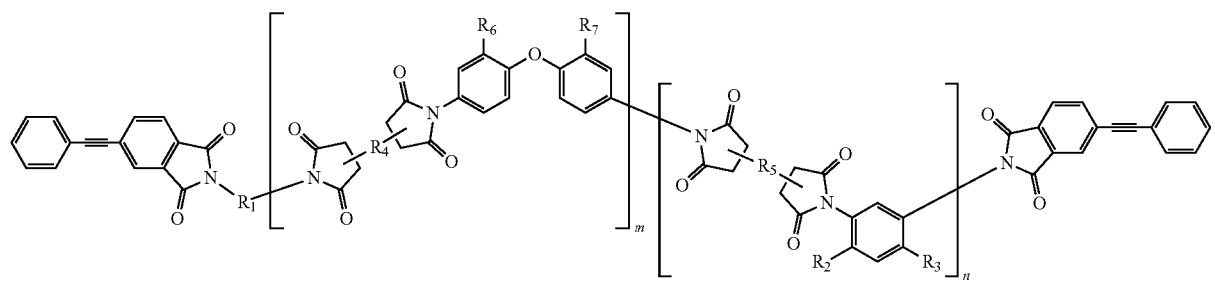

(1)

where: $R_1$ represents a divalent residue of an aromatic diamine selected from the group consisting of 2-phenyl-4,4'-diaminodiphenylether and 4-phenoxy-1,3-diaminobenzene; one of $R_2$ and $R_3$ represents a hydrogen atom and the other one of $R_2$ and $R_3$ represents a phenoxy group; $R_4$ and $R_5$ each represent a tetravalent residue of an aromatic tetracarboxylic acid and are identical or different; one of $R_6$ and $R_7$ represents a hydrogen atom and the other one of $R_6$ and $R_7$ represents a phenyl group; m and n satisfy the following: $m \geq 1$, $n > 0$, $1 < m+n \leq 10$, and $0.05 \leq m/(m+n) < 1$; and a sequence of repeating units may be a block sequence or a random sequence.

[2] The terminally modified imide oligomer described above in [1], in which: the aromatic tetracarboxylic acid is 1,2,4,5-benzenetetracarboxylic dianhydride; and the terminally modified imide oligomer is represented by the following general formula (2):

[Chem. 5]

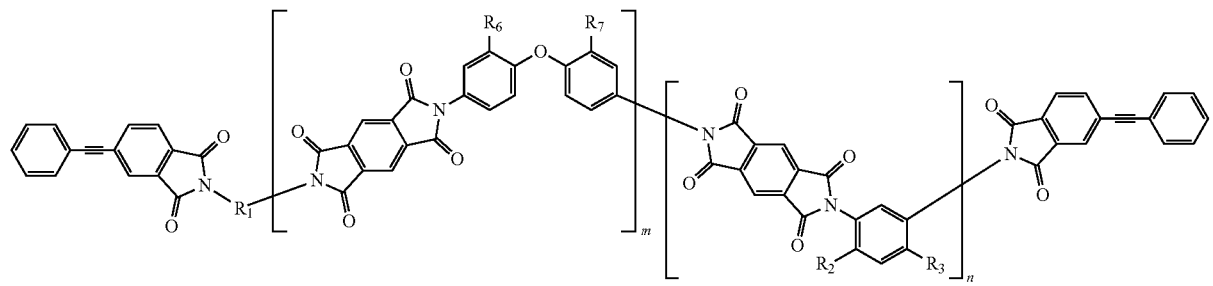

(2)

where: $R_1$ represents a divalent residue of an aromatic diamine selected from the group consisting of 2-phenyl-4,4'-diaminodiphenylether and 4-phenoxy-1,3-diaminobenzene; one of $R_2$ and $R_3$ represents a hydrogen atom and the other one of $R_2$ and $R_3$ represents a phenoxy group; one of $R_6$ and $R_7$ represents a hydrogen atom and the other one of $R_6$ and $R_7$ represents a phenyl group; m and n satisfy the following: $m \geq 1$, $n > 0$, $1 < m+n \leq 10$, and $0.05 \leq m/(m+n) < 1$; and a sequence of repeating units may be a block sequence or a random sequence.

[3] The terminally modified imide oligomer described above in [1] or [2], in which m and n satisfy the following: $0.55 \leq m/(m+n) < 1$.

[4] The terminally modified imide oligomer described above in any one of [1] to [3], in which the terminally modified imide oligomer can dissolve, in N-methyl-2-pyrrolidone which is at room temperature, so as to achieve a solid content concentration of not less than 30 weight %.

[5] A varnish obtained by dissolving a terminally modified imide oligomer described above in any one of [1] to [4] into an organic solvent.

[6] A cured product obtained by heat-curing a terminally modified imide oligomer described above in any one of [1] to [4].

[7] A cured product obtained by heat-curing a varnish described above in [5].

[8] The cured product described above in [6] or [7], in which the cured product has a glass transition temperature (Tg) of not less than 300° C.

[9] A film consisting of a cured product described above in any one of [6] to [8] and having a tensile elongation at break which is not less than 10%.

[10] An imide prepreg obtained by impregnating fibers with a varnish described above in [5] and then drying the fibers thus impregnated.

[11] The imide prepreg described above in [10], in which the imide prepreg has a resin content of 20 weight % to 50 weight %.

[12] A fiber-reinforced composite material obtained by layering and then heat-curing an imide prepreg described above in [10] or [11].

[13] A fiber-reinforced composite material obtained by layering and then heat-curing fibers to which a terminally modified imide oligomer described above in any one of [1] to [4] is adhered, the terminally modified imide oligomer being in powder form.

[14] The fiber-reinforced composite material described above in [12] or [13], wherein the fiber-reinforced composite material has a glass transition temperature (Tg) of not less than 300° C.

EXAMPLES

Some Examples will be described below for the purpose of explaining one or more embodiments of the present invention. The present invention is not, however, limited by these Examples. Characteristics were evaluated under the following conditions.

[Test Methods]

(1) 5% Weight reduction temperature measurements: Measurements were carried out with use of a thermogravimetric analysis (TGA) apparatus (EXSTAR TG/DTA6300, manufactured by Seiko Instruments), under flow of an argon gas stream and with a temperature increase rate of 5° C./min.

(2) Glass transition temperature measurements: For cured products in film form, measurements were carried out with use of a dynamic viscoelastic behavior measurement (DMA) apparatus (RSA-II, manufactured by Rheometric) with a temperature increase rate of 5° C./min and a frequency of 1 Hz. The glass transition temperature was considered to be the point of intersection of (i) a line tangent to a storage modulus of elasticity curve before a fall in the storage modulus of elasticity curve and (ii) a line tangent to the storage modulus of elasticity curve after the fall in the storage modulus of elasticity curve. For fiber-reinforced composite materials, measurements were carried out with use of a dynamic viscoelastic behavior measurement (DMA) apparatus (DMA-Q-800, manufactured by TA Instruments), using a single cantilever method, with 0.1% strain, a frequency of 1 Hz, and a temperature increase rate of 5° C./min. The glass transition temperature was considered to be the point of intersection of (i) a line tangent to a storage modulus of elasticity curve before a fall in the storage modulus of elasticity curve and (ii) a line tangent to the storage modulus of elasticity curve after the fall in the storage modulus of elasticity curve.

(3) Minimum melt viscosity measurements: Measurements were carried out with use of a rheometer (DISCOVERY HR-2, manufactured by TA Instruments) with 20 mm or 25 mm parallel plates and a temperature increase rate of 5° C./min (in Comparative Example 6, the rheometer used was the TA Instruments AR2000, with 25 mm parallel plates).

(4) Tension test (tensile modulus measurement test, tensile breaking strength measurement test, and tensile elongation at break measurement test): Measurements were made using TENSILON/UTM-II-20 (manufactured by Orientech) at room temperature, with a tensile speed of 5 mm/min. Test specimens were films having a length of 30 mm, a width of 3 mm, and a thickness of 70 μm to 160 μm.

(5) Ultrasonic flaw detection test: Measurements were carried out in water with use of a ultrasonic flaw detection imaging device (SDS-Win7800R, manufactured by Krautkramer Japan), using a 3.5 MHz flaw detection probe.

(6) Optical microscopy: Observation of cross sections of fiber-reinforced composite materials was carried out using a microscope (Axioplan2 Imaging, manufactured by Carl Zeiss Microscopy).

Example 1

To a 100 mL three-necked flask having a thermometer and a stirrer, 4.3525 g (15.8 mmol) of 2-phenyl-4,4'-diaminodiphenylether and 15.1 mL of N-methyl-2-pyrrolidone were added. After the 2-phenyl-4,4'-diaminodiphenylether was dissolved, 0.3503 g (1.75 mmol) of 4-phenoxy-1,3-diaminobenzene and 2.15 mL of N-methyl-2-pyrrolidone were added to the flask and stirred until dissolved. Next, 3.0539 g (14.0 mmol) of 1,2,4,5-benzenetetracarboxylic dianhydride and 3.0 mL of N-methyl-2-pyrrolidone were added to the flask. Nitrogen was then filled into and sealed in the flask, and a polymerization reaction was allowed to take place at room temperature for 4.5 hours so that an amide acid oligomer was produced. To the reaction solution containing the amide acid oligomer, 1.7372 g (7.00 mmol) of 4-(2-phenylethynyl)phthalic anhydride and 1.3 mL of N-methyl-2-pyrrolidone were added. Then, nitrogen was filled into and sealed in the flask, and a reaction was allowed to take place at room temperature for 1 hour so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 580 mL of ion exchange water. Powder which precipitated was separated by filtering. The powder obtained through the filtering was washed for 30 minutes with 200 mL of methanol, and then dried under reduced pressure for 3 hours at 210° C. and for 2 hours at 230° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=3.6 and n=0.4.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % remained stable, without exhibiting gelation or the like, after being left to stand at room temperature for 1 month. A solution (varnish) in which the terminally modified imide oligomer was dissolved in NMP at a concentration of 35 weight % remained stable, without exhibiting gelation or the like, after being left to stand at room temperature for 10 days. The terminally modified imide oligomer, in the form of an un-cured powder, had a minimum melt viscosity of 86 Pa·sec (348° C.). A cured product in the form of a film (thickness: 101 μm), which was obtained by heating the terminally modified imide oligomer in powder form with a hot press for 1 hour at 370° C., had a Tg (measured by DMA) of 354° C. and a 5% weight reduction temperature (determined by TGA) of 525° C. With regards to mechanical characteristics determined via a tension test, it was found that the cured product in the form of a film had a tensile modulus of 3.10 GPa, a tensile breaking strength of 125 MPa, and a tensile elongation at break which was 10%.

Example 2

To a 100 mL three-necked flask having a thermometer and a stirrer, 3.6268 g (13.1 mmol) of 2-phenyl-4,4'-diaminodiphenylether and 17.5 mL of N-methyl-2-pyrrolidone were added. After the 2-phenyl-4,4'-diaminodiphenylether was dissolved, 0.8761 g (4.38 mmol) of 4-phenoxy-1,3-diaminobenzene was added to the flask and stirred until dissolved. Next, 3.0537 g (14.0 mmol) of 1,2,4,5-benzenetetracarboxylic dianhydride was added to the flask. Nitrogen was then filled into and sealed in the flask, and a polymerization reaction was allowed to take place at room temperature for 1.5 hours so that an amide acid oligomer was produced. To the reaction solution containing the amide acid oligomer, 1.7376 g (7.00 mmol) of 4-(2-phenylethynyl)phthalic anhydride and 3.5 mL of N-methyl-2-pyrrolidone were added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 620 mL of ion exchange water. Powder which precipitated was separated by filtering. The powder obtained through the filtering was washed for 30 minutes with 100 mL of methanol and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=3 and n=1.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 35 weight % remained stable, without exhibiting gelation or the like, after being left to stand at room temperature for 1 month. The terminally modified imide oligomer, in the form of an un-cured powder, had a minimum melt viscosity of 116 Pa·sec (346° C.). A cured product in the form of a film (thickness: 90 μm), which was obtained by heating the terminally modified imide oligomer in powder form with a hot press for 1 hour at 370° C., had a Tg (measured by DMA) of 357° C. and a 5% weight reduction temperature (determined by TGA) of 517° C. With regards to mechanical characteristics determined via a tension test, it was found that the cured product in the form of a film had a tensile modulus of 2.86 GPa, a tensile breaking strength of 126 MPa, and a tensile elongation at break which was 13%.

Example 3

To a 100 mL three-necked flask having a thermometer and a stirrer, 2.4179 g (8.75 mmol) of 2-phenyl-4,4'-diaminodiphenylether and 16.3 mL of N-methyl-2-pyrrolidone were added. After the 2-phenyl-4,4'-diaminodiphenylether was dissolved, 1.7521 g (8.75 mmol) of 4-phenoxy-1,3-diaminobenzene was added to the flask and stirred until dissolved. Next, 3.0537 g (14.0 mmol) of 1,2,4,5-benzenetetracarboxylic dianhydride and 2 mL of N-methyl-2-pyrrolidone were added to the flask. Nitrogen was then filled into and sealed in the flask, and a polymerization reaction was allowed to take place at room temperature for 1.5 hours so that an amide acid oligomer was produced. To the reaction solution containing the amide acid oligomer, 1.7376 g (7.00 mmol) of 4-(2-phenylethynyl)phthalic anhydride and 2 mL of N-methyl-2-pyrrolidone were added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 600 mL of ion exchange water. Powder which precipitated was separated by filtering. The powder obtained through the filtering was washed for 30 minutes with 100 mL of methanol and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=2 and n=2.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 35 weight % remained stable, without exhibiting gelation or the like, after being left to stand at room temperature for 1 month. The terminally modified imide oligomer, in the form of an un-cured powder, had a minimum melt viscosity of 102 Pa·sec (348° C.). A cured product in the form of a film (thickness: 84 μm), which was obtained by heating the terminally modified imide oligomer in powder form with a hot press for 1 hour at 370° C., had a Tg (measured by DMA) of 364° C. and a 5% weight reduction temperature (determined by TGA) of 516° C. With regards to mechanical characteristics determined via a tension test, it was found that the cured product in the form of a film had a tensile modulus of 2.85 GPa, a tensile breaking strength of 121 MPa, and a tensile elongation at break which was 10%.

Example 4

To a 100 mL three-necked flask having a thermometer and a stirrer, 1.2089 g (4.37 mmol) of 2-phenyl-4,4'-diaminodiphenylether and 16 mL of N-methyl-2-pyrrolidone were added. After the 2-phenyl-4,4'-diaminodiphenylether was dissolved, 2.6282 g (13.1 mmol) of 4-phenoxy-1,3-diaminobenzene and 1 mL of N-methyl-2-pyrrolidone were added to the flask and stirred until dissolved. Next, 3.0537 g (14.0 mmol) of 1,2,4,5-benzenetetracarboxylic dianhydride and 2 mL of N-methyl-2-pyrrolidone were added to the flask. Nitrogen was then filled into and sealed in the flask, and a polymerization reaction was allowed to take place at room temperature for 1.5 hours so that an amide acid oligomer was produced. To the reaction solution containing the amide acid oligomer, 1.7376 g (7.00 mmol) of 4-(2-phenylethynyl) phthalic anhydride and 0.5 mL of N-methyl-2-pyrrolidone were added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 580 mL of ion exchange water. Powder which precipitated was separated by filtering. The powder obtained through the filtering was washed for 30 minutes with 100 mL of methanol and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=1 and n=3.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % gelated after being left to stand at room temperature for a number of days, but returned to a solution form upon being heated again to 80° C. This solution was again left to stand at room temperature, and gelation was observed again after a number of days. The terminally modified imide oligomer, in the form of an un-cured powder, had a minimum melt viscosity of 107 Pa·sec (346° C.). A cured product in the form of a film (thickness: 88 μm), which was obtained by heating the terminally modified imide oligomer in powder form with a hot press for 1 hour at 370° C., had a Tg (measured by DMA) of 366° C. and a 5% weight reduction temperature (determined by TGA) of 516° C. With regards to mechanical characteristics determined via a tension test, it was found that the cured product in the form of a film had a tensile modulus of 2.83 GPa, a tensile breaking strength of 122 MPa, and a tensile elongation at break which was 11%.

Comparative Example 1

To a 100 mL three-necked flask having a thermometer and a stirrer, 3.5042 g (17.5 mmol) of 4-phenoxy-1,3-diaminobenzene and 15 mL of N-methyl-2-pyrrolidone were added and stirred until dissolved. Next, 3.0537 g (14.0 mmol) of 1,2,4,5-benzenetetracarboxylic dianhydride and 1.5 mL of N-methyl-2-pyrrolidone were added to the flask. Nitrogen was then filled into and sealed in the flask, and a polymerization reaction was allowed to take place at room temperature for 1.5 hours so that an amide acid oligomer was produced. To the reaction solution containing the amide acid oligomer, 1.7376 g (7.00 mmol) of 4-(2-phenylethynyl) phthalic anhydride and 2.3 mL of N-methyl-2-pyrrolidone were added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 550 mL of ion exchange water. Powder which precipitated was separated by filtering. The powder obtained through the filtering was washed for 30 minutes with 100 mL of methanol and then dried under reduced pressure for 14 hours at 200° C., so that a terminally modified imide oligomer was obtained.

The terminally modified imide oligomer was composed such that, in the above general formula (2), $R_1$ was represented by a 4-phenoxy-1,3-diaminobenzene residue, and, on average, m=0 and n=4.

The terminally modified imide oligomer, in the form of an un-cured powder, had a solubility, in an NMP solvent which was at room temperature, such that concentration was less than 10 weight %. The terminally modified imide oligomer, in the form of an un-cured powder, had a minimum melt viscosity of 127 Pa·sec (359° C.). A cured product in the form of a film (thickness: 84 μm), which was obtained by heating the terminally modified imide oligomer in powder form with a hot press for 1 hour at 370° C., had a Tg (measured by DMA) of 357° C. and a 5% weight reduction temperature (determined by TGA) of 515° C. With regards to mechanical characteristics determined via a tension test, it was found that the cured product in the form of a film had a tensile modulus of 2.80 GPa, a tensile breaking strength of 109 MPa, and a tensile elongation at break which was 7%.

Comparative Example 2

To a 100 mL three-necked flask having a thermometer and a stirrer, 4.8358 g (17.5 mmol) of 2-phenyl-4,4'-diaminodiphenylether and 17.5 mL of N-methyl-2-pyrrolidone were added and stirred until dissolved. Next, 3.0537 g (14.0 mmol) of 1,2,4,5-benzenetetracarboxylic dianhydride and 2.2 mL of N-methyl-2-pyrrolidone were added to the flask. Nitrogen was then filled into and sealed in the flask, and a polymerization reaction was allowed to take place at room temperature for 6 hours so that an amide acid oligomer was produced. To the reaction solution containing the amide acid oligomer, 1.7376 g (7.00 mmol) of 4-(2-phenylethynyl) phthalic anhydride and 2.2 mL of N-methyl-2-pyrrolidone were added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was diluted to 15 weight % and then introduced into 640 mL of ion exchange water. Powder which precipitated was separated by filtering. The powder obtained through the filtering was washed for 30 minutes with 100 mL of methanol and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue, and, on average, m=4 and n=0.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % gelated after being left to stand at room temperature for a number of days, but returned to a solution form upon being heated again to 80° C. This solution was again left to stand at room temperature, and gelation was observed again after a number of days. The terminally modified imide oligomer, in the form of an un-cured powder, had a minimum melt viscosity of 114 Pa·sec (351° C.). A cured product in the form of a film (thickness: 78 μm), which was obtained by heating the terminally modified imide oligomer in powder form with a hot press for 1 hour at 370° C., had a Tg (measured by DMA) of 348° C. and a 5% weight reduction temperature (determined by TGA) of 527° C. With regards to mechanical characteristics determined via a tension test, it was found that the cured product in the form of a film had a tensile modulus of 2.98 GPa, a tensile breaking strength of 127 MPa, and a tensile elongation at break which was 14° %.

Comparative Example 3

To a 100 mL three-necked flask having a thermometer and a stirrer, 3.7305 g (13.5 mmol) of 2-phenyl-4,4'-diaminodiphenylether, 0.1622 g (1.5 mmol) of 1,3-diaminobenzene, and 14.5 mL of N-methyl-2-pyrrolidone were added and stirred until dissolved. Next, 2.6174 g (12.0 mmol) of 1,2,4,5-benzenetetracarboxylic dianhydride and 3.0 mL of N-methyl-2-pyrrolidone were added to the flask. Nitrogen was then filled into and sealed in the flask, and a reaction was allowed to take place at room temperature for 2 hours, and at 40° C. for 1 hour. Thereafter, a polymerization reaction was allowed to take place at room temperature for 13 hours so that an amide acid oligomer was produced. To the reaction solution containing the amide acid oligomer, 1.4894 g (6.00 mmol) of 4-(2-phenylethynyl)phthalic anhydride and 0.6 mL of N-methyl-2-pyrrolidone were added. Then, nitrogen was filled into and sealed in the flask, and a reaction was allowed to take place at room temperature for 1 hour so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was diluted to 15 weight % and then introduced into 530 mL of ion exchange water. Powder which precipitated was separated by filtering. The powder obtained through the filtering was washed for 15 minutes with 100 mL of methanol and then dried under reduced pressure for 5 hours at 220° C., so that a terminally modified imide oligomer was obtained. The terminally modified imide oligomer was composed such that, in the above general formula (2), $R_1$ was represented by a 2-phenyl-4,4'-diaminodiphenylether residue or a 1,3-diaminobenzene residue, $R_2$ and $R_3$ were each represented by a hydrogen atom, and, on average, m=3.6 and n=0.4.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % remained stable, without exhibiting gelation or the like, after being left to stand at room temperature for 1 month. A solution (varnish) in which the terminally modified imide oligomer was dissolved in NMP at a concentration of 35 weight % gelated after being left to stand at room temperature for a number of days, but returned to a solution form upon being heated again to 80° C. This solution was again left to stand at room temperature, and gelation was observed again after a number of days. The terminally modified imide oligomer, in the form of an un-cured powder, had a minimum melt viscosity of 147 Pa·sec (348° C.). A cured product in the form of a film (thickness: 92 μm), which was obtained by heating the terminally modified imide oligomer in powder form with a hot press for 1 hour at 370° C., had a Tg (measured by DMA) of 353° C. and a 5% weight reduction temperature (determined by TGA) of 531° C. With regards to mechanical characteristics determined via a tension test, it was found that the cured product in the form of a film had a tensile modulus of 2.97 GPa, a tensile breaking strength of 125 MPa, and a tensile elongation at break which was 10%.

Comparative Example 4

To a 100 mL three-necked flask having a thermometer and a stirrer, 3.1087 g (11.2 mmol) of 2-phenyl-4,4'-diaminodiphenylether and 0.4055 g (3.75 mmol) of 1,3-diaminobenzene were added. Thereafter, 15 mL of N-methyl-2-pyrrolidone was added, and the contents of the flask were stirred until dissolved. Next, 2.6174 g (12.0 mmol) of 1,2,4,5-benzenetetracarboxylic dianhydride and 1 mL of N-methyl-2-pyrrolidone were added to the flask. Nitrogen was then filled into and sealed in the flask, and a polymerization reaction was allowed to take place at room temperature for 1.5 hours so that an amide acid oligomer was produced. To the reaction solution containing the amide acid oligomer, 1.4894 g (6.00 mmol) of 4-(2-phenylethynyl)phthalic anhydride and 1.5 mL of N-methyl-2-pyrrolidone were added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. Gelation was observed when the reaction solution was cooled to a temperature below 180° C. The reaction solution was then diluted to 15 weight % and stirred at 180° C. Thereafter, when the reaction solution was cooled, no gelation was observed at temperatures of 60° C. or greater. The reaction solution was introduced into 510 mL of ion exchange water in a manner such that the temperature of the reaction solution did not fall to 60° C. or lower. Powder which precipitated was separated by filtering. The powder obtained through the filtering was washed for 30 minutes with 100 mL of methanol and then dried under reduced pressure for 14 hours at 150° C., so that a terminally modified imide oligomer was obtained. The terminally modified imide oligomer was composed such that, in the above general formula (2), $R_1$ was represented by a 2-phenyl-4,4'-diaminodiphenylether residue or a 1,3-diaminobenzene residue, $R_2$ and $R_3$ were each represented by a hydrogen atom, and, on average, m=3 and n=1.

The terminally modified imide oligomer, in the form of an un-cured powder, had a solubility, in an NMP solvent which was at room temperature, such that concentration was less than 10 weight %. The terminally modified imide oligomer, in the form of an un-cured powder, had a minimum melt viscosity of 615 Pa·sec (360° C.). A cured product in the form of a film (thickness: 84 μm), which was obtained by heating the terminally modified imide oligomer in powder form with a hot press for 1 hour at 370° C., had a Tg (measured by DMA) of 358° C. and a 5% weight reduction temperature (determined by TGA) of 525° C. With regards to mechanical characteristics determined via a tension test, it was found that the cured product in the form of a film had a tensile modulus of 2.92 GPa, a tensile breaking strength of 125 MPa, and a tensile elongation at break which was 11%.

Comparative Example 5

To a 100 mL three-necked flask having a thermometer and a stirrer, 2.0725 g (7.50 mmol) of 2-phenyl-4,4'-diaminodiphenylether and 0.8111 g (7.50 mmol) of 1,3-diaminobenzene were added. Thereafter, 15 mL of N-methyl-2-pyrrolidone was added, and the contents of the flask were stirred until dissolved. Next, 2.6174 g (12.0 mmol) of 1,2,4,5-benzenetetracarboxylic dianhydride and 3.0 mL of N-methyl-2-pyrrolidone were added to the flask. Nitrogen was then filled into and sealed in the flask, and a reaction was allowed to take place at room temperature for 50 minutes. Thereafter, a polymerization reaction was allowed to take place at 60° C. for 20 minutes so that an amide acid oligomer was produced. To the reaction solution containing the amide acid oligomer, 1.4894 g (6.00 mmol) of 4-(2-phenylethynyl)phthalic anhydride was added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream at 180° C. so that imide bonds were formed in the terminally modified amide acid oligomer. After 3.5 hours, the reaction was stopped because gelation of the reaction solution was observed. The reaction solution was diluted to 14 weight % and then introduced into 480 mL of ion exchange water. Powder which precipitated was separated by filtering. The powder obtained through the filtering was washed for 30 minutes with 100 mL of methanol and then dried under reduced pressure for 14 hours at 100° C., so that a terminally modified imide oligomer was obtained. The terminally modified imide oligomer was composed such that, in the above general formula (2), $R_1$ was represented by a 2-phenyl-4,4'-diaminodiphenylether residue or a 1,3-diaminobenzene residue, $R_2$ and $R_3$ were each represented by a hydrogen atom, and, on average, m=2 and n=2.

The terminally modified imide oligomer, in the form of an un-cured powder, had a solubility, in an NMP solvent which was at room temperature, such that concentration was less than 10 weight %. A favorable cured product in the form of a film could not be obtained because the terminally modified imide oligomer in powder form did not exhibit sufficient melt flowability even at a temperature of 300° C. or more.

Example 5

To a 100 mL three-necked flask having a thermometer and a stirrer, 4.9739 g (18.0 mmol) of 2-phenyl-4,4'-diaminodiphenylether and 1.2014 g (6.00 mmol) of 4-phenoxy-1,3-diaminobenzene were added. Thereafter, 22 mL of N-methyl-2-pyrrolidone was added, and the contents of the flask were stirred until dissolved. Next, 4.5805 g (21.0 mmol) of 1,2,4,5-benzenetetracarboxylic dianhydride and 2 mL of N-methyl-2-pyrrolidone were added to the flask. Nitrogen was then filled into and sealed in the flask, and a polymerization reaction was allowed to take place at room temperature for 1 hour so that an amide acid oligomer was produced. To the reaction solution containing the amide acid oligomer, 1.4894 g (6.00 mmol) of 4-(2-phenylethynyl) phthalic anhydride and 3.8 mL of N-methyl-2-pyrrolidone were added. Then, nitrogen was filled into and sealed in the flask, and a reaction was allowed to take place at room temperature for 4 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 820 mL of ion exchange water. Powder which precipitated was separated by filtering. The powder obtained through the filtering was washed for 30 minutes with 150 mL of ion exchange water, washed for 30 minutes with 150 mL of methanol, and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=5.25 and n=1.75.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % remained stable, without exhibiting gelation or the like, after being left to stand at room temperature for 1 month. The terminally modified imide oligomer, in the form of an un-cured powder, had a minimum melt viscosity of 1,341 Pa·sec (365° C.). A cured product in the form of a film (thickness: 122 µm), which was obtained by heating the terminally modified imide oligomer in powder form with a hot press for 1 hour at 370° C., had a Tg (measured by DMA) of 342° C. and a 5% weight reduction temperature (determined by TGA) of 518° C. With regards to mechanical characteristics determined via a tension test, it was found that the cured product in the form of a film had a tensile modulus of 3.10 GPa, a tensile breaking strength of 128 MPa, and a tensile elongation at break which was 15%.

Example 6

To a 100 mL three-necked flask having a thermometer and a stirrer, 2.0024 g (10.0 mmol) of 4-phenoxy-1,3-diaminobenzene and 17 mL of N-methyl-2-pyrrolidone were added. After the 4-phenoxy-1,3-diaminobenzene was dissolved, 2.7633 g (10.0 mmol) of 2-phenyl-4,4'-diaminodiphenylether and 2 mL of N-methyl-2-pyrrolidone were added to the flask and stirred until dissolved. Next, 3.8171 g (17.5 mmol) of 1,2,4,5-benzenetetracarboxylic dianhydride and 2 mL of N-methyl-2-pyrrolidone were added to the flask. Nitrogen was then filled into and sealed in the flask, and a polymerization reaction was allowed to take place at room temperature for 1.5 hours so that an amide acid oligomer was produced. To the reaction solution containing the amide acid oligomer, 1.2412 g (5.00 mmol) of 4-(2-phenylethynyl)phthalic anhydride and 1.3 mL of N-methyl-2-pyrrolidone were added. Then, nitrogen was filled into and sealed in the flask, and a reaction was allowed to take place at room temperature for 1.5 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 660 mL of ion exchange water. Powder which precipitated was separated by filtering. The powder obtained through the filtering was washed for 30 minutes with 100 mL of methanol and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=3.5 and n=3.5.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % remained stable, without exhibiting gelation or the like, after being left to stand at room temperature for 1 month. The terminally modified imide oligomer, in the form of an un-cured powder, had a minimum melt viscosity of 1,010 Pa·sec (363° C.). A cured product in the form of a film (thickness: 133 µm), which was obtained by heating the terminally modified imide oligomer in powder form with a hot press for 1 hour at 370° C., had a Tg (measured by DMA) of 357° C. and a 5% weight reduction temperature (determined by TGA) of 522° C. With regards to mechanical characteristics determined via a tension test, it was found that the cured product in the form of a film had a tensile modulus of 2.91 GPa, a tensile breaking strength of 125 MPa, and a tensile elongation at break which was 17%.

Comparative Example 6

To a 1000 mL separable flask having a thermometer and a nitrogen introduction tube, 83.56 g (302.4 mmol) of 2-phenyl-4,4'-diaminodiphenylether and 11.71 g (33.6 mmol) of 9,9-bis(4-aminophenyl)fluorene were added. Thereafter, 359 mL of N-methyl-2-pyrrolidone was added, and the contents of the flask were stirred until dissolved. Next, 62.82 g (288 mmol) of 1,2,4,5-benzenetetracarboxylic dianhydride was added to the flask. Thereafter, under flow of a nitrogen gas stream, a polymerization reaction was allowed to take place at room temperature for 3 hours, at 60 degrees for 1 hour, and at 80 degrees for 2 hours so that an amide acid oligomer was produced. The reaction solution containing the amide acid oligomer was cooled to room temperature, and then 23.83 g (96 mmol) of 4-(2-phenylethynyl)phthalic anhydride was added. Then, under flow of a nitrogen gas stream, a reaction was allowed to take place at room temperature for 15 hours so that the amide acid oligomer was terminally modified. Thereafter, stirring was performed under flow of a nitrogen gas stream for 5 hours at 195° C. so that imide bonds were formed in the terminally modified amide acid oligomer. The reaction solution was cooled. Then, 10.43 g of the reaction solution was diluted to 5 weight % and then introduced into 900 mL of ion exchange water. Powder which precipitated was separated by filtering. The powder obtained through the filtering was washed with methanol and then dried under reduced pressure for 4 hours at 240° C., so that a terminally modified imide oligomer was obtained. The terminally modified imide oligomer was composed such that, in the following general formula (3), $R_8$ was represented by a 2-phenyl-4,4'-diaminodiphenylether residue or a 9,9-bis(4-aminophenyl)fluorene residue, one of $R_9$ and $R_{10}$ represented a hydrogen atom, the other one of $R_9$ and $R_{10}$ represented a phenyl group, and, on average, m=5.4 and n=0.6.

[Chem. 6]

(3)

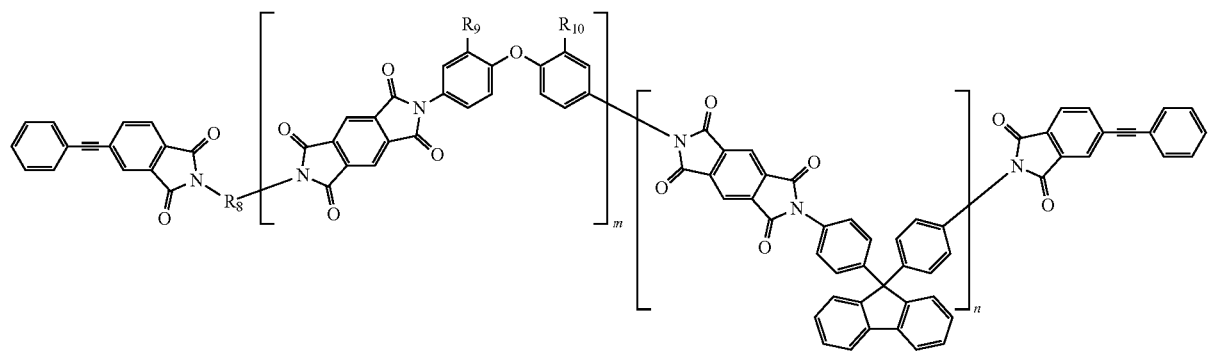

The terminally modified imide oligomer, in the form of an un-cured powder, was able to be dissolved, into an NMP solvent which was at room temperature, so as to achieve a concentration of not less than 30 weight %. The terminally modified imide oligomer, in the form of an un-cured powder, had a minimum melt viscosity of 9,631 Pa-sec (346° C.). A cured product in the form of a film (thickness: 100 μm), which was obtained by heating the terminally modified imide oligomer in powder form with a hot press for 1 hour at 370° C., had a Tg (measured by DMA) of 355° C. With regards to mechanical characteristics determined via a tension test, it was found that the cured product in the form of a film had a tensile modulus of 2.67 GPa, a tensile breaking strength of 128 MPa, and a tensile elongation at break which was 15%.

Example 7

To a 100 mL three-necked flask having a thermometer and a stirrer, 4.5594 g (16.5 mmol) of 2-phenyl-4,4'-diaminodiphenylether and 1.1013 g (5.50 mmol) of 4-phenoxy-1,3-diaminobenzene were added. Thereafter, 20 mL of N-methyl-2-pyrrolidone was added, and the contents of the flask were stirred until dissolved. Next, 4.3624 g (20.0 mmol) of 1,2,4,5-benzenetetracarboxylic dianhydride and 2.5 mL of N-methyl-2-pyrrolidone were added to the flask. Nitrogen was then filled into and sealed in the flask, and a polymerization reaction was allowed to take place at room temperature for 1 hour so that an amide acid oligomer was produced. To the reaction solution containing the amide acid oligomer, 0.9929 g (4.00 mmol) of 4-(2-phenylethynyl) phthalic anhydride and 2.5 mL of N-methyl-2-pyrrolidone were added. Then, nitrogen was filled into and sealed in the flask, and a reaction was allowed to take place at room temperature for 1 hour so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 10 weight %, and then introduced into 1,100 mL of ion exchange water. Powder which precipitated was separated by filtering. The powder obtained through the filtering was washed for 30 minutes with 150 mL of ion exchange water, washed for 30 minutes with 150 mL of methanol, and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=7.5 and n=2.5.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % remained stable, without exhibiting gelation or the like, after being left to stand at room temperature for 1 month. The terminally modified imide oligomer, in the form of an un-cured powder, had a minimum melt viscosity of 7,087 Pa-sec (365° C.). A cured product in the form of a film (thickness: 160 μm), which was obtained by heating the terminally modified imide oligomer in powder form with a hot press for 1 hour at 385° C., had a Tg (measured by DMA) of 360° C. and a 5% weight reduction temperature (determined by TGA) of 523° C. With regards to mechanical characteristics determined via a tension test, it was found that the cured product in the form of a film had a tensile modulus of 2.98 GPa, a tensile breaking strength of 123 MPa, and a tensile elongation at break which was 12%.

Example 8

To a 100 mL three-necked flask having a thermometer and a stirrer, 3.0396 g (11.0 mmol) of 2-phenyl-4,4'-diaminodiphenylether and 2.2026 g (11.0 mmol) of 4-phenoxy-1,3-diaminobenzene were added. Thereafter, 19 mL of N-methyl-2-pyrrolidone was added, and the contents of the flask were stirred until dissolved. Next, 4.3624 g (20.0 mmol) of 1,2,4,5-benzenetetracarboxylic dianhydride and 2.5 mL of N-methyl-2-pyrrolidone were added to the flask. Nitrogen was then filled into and sealed in the flask, and a polymerization reaction was allowed to take place at room temperature for 1 hour so that an amide acid oligomer was produced. To the reaction solution containing the amide acid oligomer, 0.9929 g (4.00 mmol) of 4-(2-phenylethynyl) phthalic anhydride and 2.5 mL of N-methyl-2-pyrrolidone were added. Then, nitrogen was filled into and sealed in the flask, and a reaction was allowed to take place at room temperature for 3 hours so that the amide acid oligomer was terminally modified. Thereafter, a nitrogen introduction tube was attached to the flask, and stirring was performed under flow of a nitrogen gas stream for 5 hours at 180° C. so that imide bonds were formed in the terminally modified amide acid oligomer. The reaction solution was cooled, diluted to 15 weight %, and then introduced into 700 mL of ion exchange water. Powder which precipitated was separated by filtering. The powder obtained through the filtering was washed for 30 minutes with 150 mL of ion exchange water, washed for 30 minutes with 150 mL of methanol, and then dried under reduced pressure for 14 hours at 200° C., so that a terminally modified imide oligomer was obtained. The terminally modified imide oligomer was composed such that, in the above general formula (2), $R_1$ was represented by a 2-phenyl-4,4'-diaminodiphenylether residue or a 4-phenoxy-1,3-diaminobenzene residue, and, on average, m=5 and n=5.

The terminally modified imide oligomer, in the form of an un-cured powder, was able to be dissolved, into an NMP solvent which was at room temperature, so as to achieve a concentration of not less than 30 weight %. A solution (varnish) in which the terminally modified imide oligomer was dissolved in NMP at a concentration of 30 weight % remained stable, without exhibiting gelation or the like, after being left to stand at room temperature for 1 month. The terminally modified imide oligomer, in the form of an un-cured powder, had a minimum melt viscosity of 11,962 Pa-sec (382° C.). A cured product in the form of a film (thickness: 115 μm), which was obtained by heating the terminally modified imide oligomer in powder form with a hot press for 1 hour at 385° C., had a Tg (measured by DMA) of 364° C. and a 5% weight reduction temperature (determined by TGA) of 519° C. With regards to mechanical characteristics determined via a tension test, it was found that the cured product in the form of a film had a tensile modulus of 3.00 GPa, a tensile breaking strength of 123 MPa, and a tensile elongation at break which was 16%.

Example 9

First prepared was a solution (varnish) in which a terminally modified imide oligomer produced in the same manner as in Example 2 (specifically, a terminally modified imide oligomer composed such that, in the above general formula (2), $R_1$ is represented by a 2-phenyl-4,4'-diaminodiphenylether residue or a 4-phenoxy-1,3-diaminobenzene residue and, on average, m=3 and n=1) was dissolved in N-methyl-2-pyrrolidone (such that a solid content concentration was 35 weight %). This solution was impregnated into a 12.5 cm×12.5 cm plain-woven carbon fiber material (W-6E01 (IMS60 6K), manufactured by Toho Tenax; fiber mass per unit area: 193 g/m²), which had been priorly subjected to de-sizing with use of acetone. After being impregnated thusly, the plain-woven carbon fiber material was dried for 10 minutes at 150° C. so that an imide prepreg was obtained. The imide prepreg had a resin content of 34 weight % and a residual volatile component content of 9%.

Onto a 45 cm×45 cm stainless steel plate, a polyimide film was placed to serve as a separation film. Eight layers of the imide prepreg were layered onto the polyimide film. Another polyimide film and another stainless steel plate were placed thereupon, and the stack was heated on a hot press under vacuum. Specifically, the temperature was increased at a rate of 5° C./min until 260° C. was reached, the stack was heated at 260° C. for 2 hours, and then the temperature was again increased at a rate of 4° C./min until 288° C. was reached. The stack was kept at 288° C. for 40 minutes. Thereafter, a pressure of 1.4 MPa was applied, and the temperature was increased at a rate of 4° C./min until 370° C. was reached. The temperature of 370° C. and the pressure of 1.4 MPa were then maintained for 1 hour. It was found, from the appearance of the resulting laminate, from the results of an ultrasonic flaw detection test, and from the results of a cross section observation test, that the laminate was a carbon fiber composite material (fiber-reinforced composite material) in which resin had been impregnated favorably. The laminate had a glass transition temperature of 373° C. and a calculated fiber volume fraction (Vf) of 0.59.

[Explanation of Results]

From the results of Examples 1, 2, and 3, and the results of Comparative Example 2, it was found that the terminally modified imide oligomer of one or more embodiments of the present invention, which contains aromatic diamines including 2-phenyl-4,4'-diaminodiphenylether and 4-phenoxy-1,3-diaminobenzene, exhibits improved in-solution storage stability and improved glass transition temperature (Tg) as a cured product, while also maintaining a low melt viscosity exhibited by a terminally modified imide oligomer which uses only 2-phenyl-4,4'-diaminodiphenylether as an aromatic diamine.

Furthermore, from the results of Examples 1, 2, and 3, and the results of Comparative Examples 3, 4, and 5, it was found that the terminally modified imide oligomer of one or more embodiments of the present invention, which contains aromatic diamines including 2-phenyl-4,4'-diaminodiphenylether and 4-phenoxy-1,3-diaminobenzene, exhibits improved solubility in an organic solvent, improved in-solution storage stability, and improved moldability, as compared to a terminally modified imide oligomer which uses 2-phenyl-4,4'-diaminodiphenylether and 1,3-diaminobenzene as aromatic diamines.

Examples 1, 2, 3, 5, 6, 7, and 8, in which m and n satisfied 0.5≤m/(m+n)<1, each exhibited a greater improvement in in-solution storage stability than Example 4, in which m and n satisfied m/(m+n)=0.25.

Furthermore, Examples 5 and 6, in which aromatic diamines including 2-phenyl-4,4'-diaminodiphenylether and 4-phenoxy-1,3-diaminobenzene were used, exhibited markedly lower melt viscosity in comparison to Comparative Example 6, in which 2-phenyl-4,4'-diaminodiphenylether and 9,9-bis(4-aminophenyl)fluorene were used as aromatic diamines.

Furthermore, as illustrated by Example 9, it was found that using the terminally modified imide oligomer of Example 2 made it possible to obtain a fiber-reinforced composite material having a high heat resistance.

One or more embodiments of the present invention relate to a material that can be used in a wide range of fields requiring easy moldability and high heat resistance, such as the fields of aircraft and space industry devices.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A terminally modified imide oligomer represented by the following general formula:

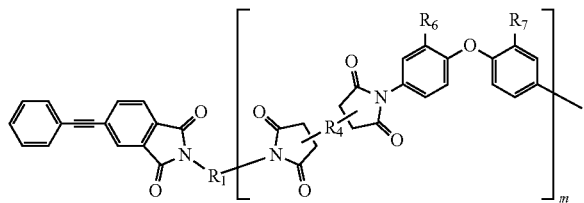

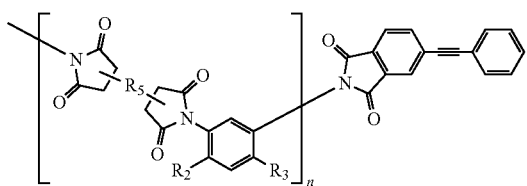

wherein
R₁ is a divalent residue of an aromatic diamine selected from the group consisting of 2-phenyl-4,4'-diaminodiphenylether and 4-phenoxy-1,3-diaminobenzene,
R₂ and R₃ are different from each other and are each selected from the group consisting of a hydrogen atom and a phenoxy group,
R₄ and R₅ are identical to or different from each other and are each a tetravalent residue of an aromatic tetracarboxylic acid,
R₆ and R₇ are different from each other and are each selected from the group consisting of a hydrogen atom and a phenyl group,
m and n satisfy the following:
m≥1;
n>0;
1<m+n≤10; and
0.05≤m/(m+n)<1, and
a sequence of repeating units is a block sequence or a random sequence.

2. The terminally modified imide oligomer according to claim 1, wherein
R₄ and R₅ are identical to each other,
the aromatic tetracarboxylic acid is 1,2,4,5-benzenetetracarboxylic dianhydride, and
the general formula is represented by the following:

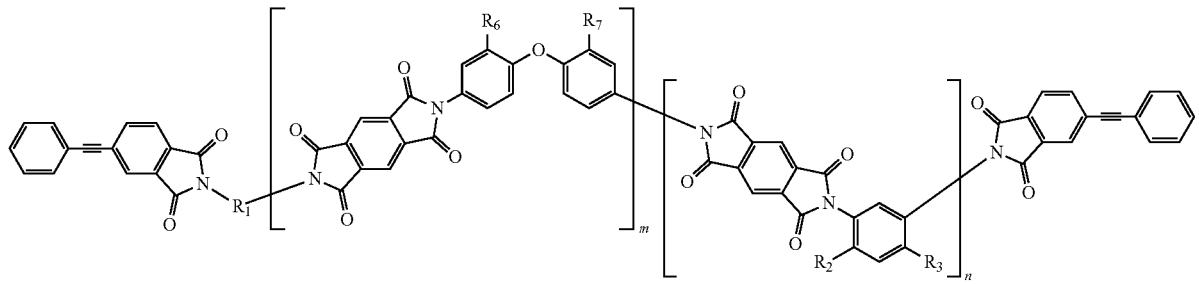

3. The terminally modified imide oligomer according to claim 1, wherein m and n satisfy 0.5≤m/(m+n)<1.

4. The terminally modified imide oligomer according to claim 1, wherein the terminally modified imide oligomer is soluble in N-methyl-2-pyrrolidone at room temperature at a solid content concentration of 30 weight % or more.

5. A varnish obtained by dissolving the terminally modified imide oligomer according to claim 1 into an organic solvent.

6. A cured product obtained by heat-curing the terminally modified imide oligomer according to claim 1.

7. A cured product obtained by heat-curing the varnish according to claim 5.

8. The cured product according to claim 6, wherein the cured product has a glass transition temperature (Tg) of 300° C. or more.

9. A film consisting of the cured product according to claim 6, wherein the film has a tensile elongation at break of 10% or more.

10. An imide prepreg obtained by impregnating fibers with the varnish according to claim 5 and then drying the impregnated fibers.

11. The imide prepreg according to claim 10, wherein the imide prepreg has a resin content of 20 to 50 weight %.

12. A fiber-reinforced composite material obtained by layering and then heat-curing the imide prepreg according to claim 10.

13. A fiber-reinforced composite material obtained by layering and then heat-curing fibers, wherein the terminally modified imide oligomer according to claim 1 is adhered to the fibers, the terminally modified imide oligomer being in powder form.

14. The fiber-reinforced composite material according to claim 12, wherein the fiber-reinforced composite material has a glass transition temperature (Tg) of 300° C. or more.

* * * * *